United States Patent [19]

Durand

[11] Patent Number: 4,504,269

[45] Date of Patent: Mar. 12, 1985

[54] DEVICE FOR CATHETERIZATION IN PARTICULAR FOR PERFUSIONS IN THE MEDICAL AND VETERINARY FIELDS

[76] Inventor: Alain J. Durand, Parc à Ballons, Résidence Oméga, F-34000 Montpellier, France

[21] Appl. No.: 471,211

[22] Filed: Mar. 1, 1983

[30] Foreign Application Priority Data

Mar. 5, 1982 [FR] France ............................... 82 03674

[51] Int. Cl.³ .............................................. A61M 5/00
[52] U.S. Cl. ..................................... 604/272; 604/283
[58] Field of Search ............... 604/272, 274, 280, 283, 604/273, 164, 165, 264; 128/339; 285/256

[56] References Cited

U.S. PATENT DOCUMENTS

| | | | |
|---|---|---|---|
| 2,908,053 | 10/1959 | Morrow | 285/256 X |
| 3,345,090 | 10/1967 | Weatherhead et al. | 285/256 |
| 3,861,393 | 1/1975 | Durand | 285/256 |
| 4,140,125 | 2/1979 | Smith | 128/339 X |
| 4,359,053 | 11/1982 | Benjamin | 128/339 |
| 4,405,312 | 9/1983 | Gross | 604/283 X |

Primary Examiner—Stephen C. Pellegrino
Attorney, Agent, or Firm—Young & Thompson

[57] ABSTRACT

A needle for "tunnelization" beneath a patient's skin and subsequent perfusion is attached to a flexible catheter tube by means of a fastening device comprising a rigid tube having the same internal diameter as the flexible tube. A needle constriction serves to clamp the end of the flexible tube against the rigid tube without producing any reduction in internal diameter of the flexible tube.

3 Claims, 9 Drawing Figures

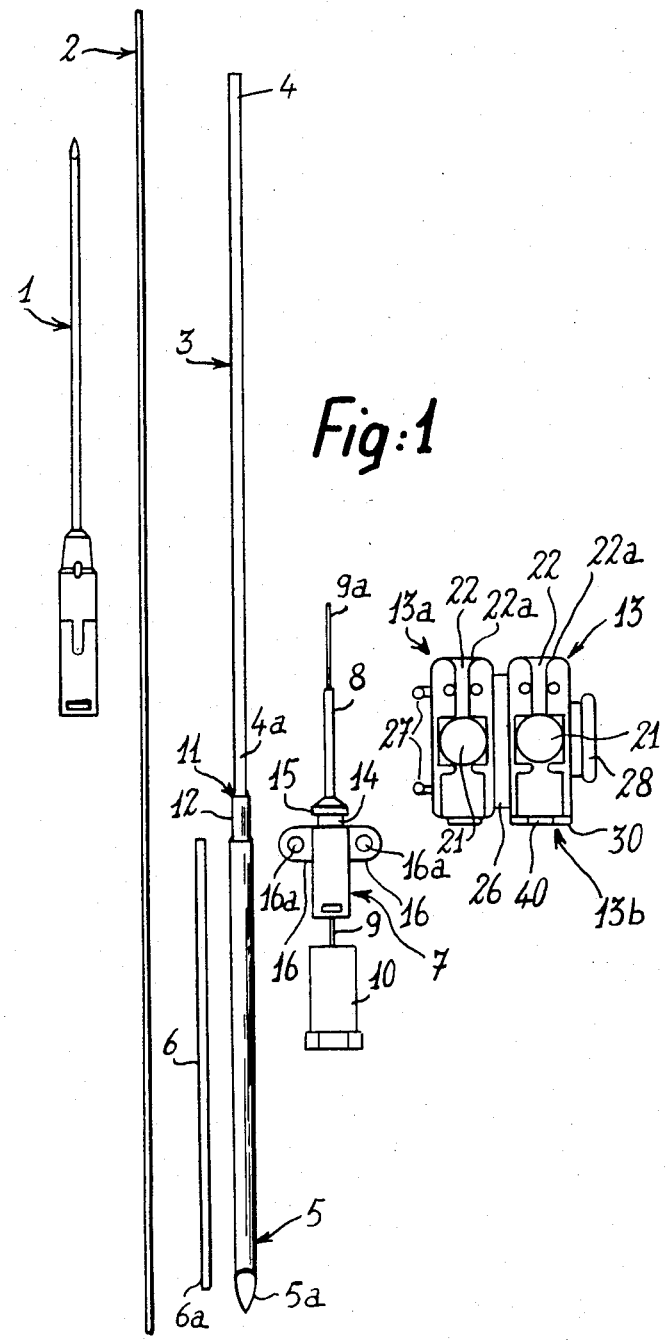
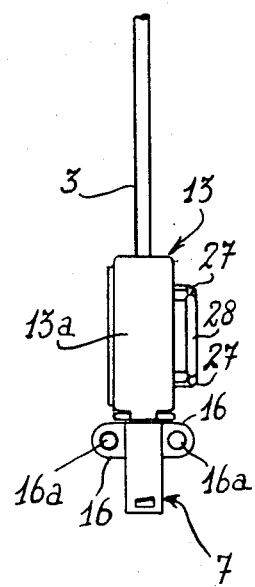
Fig:1
Fig:8

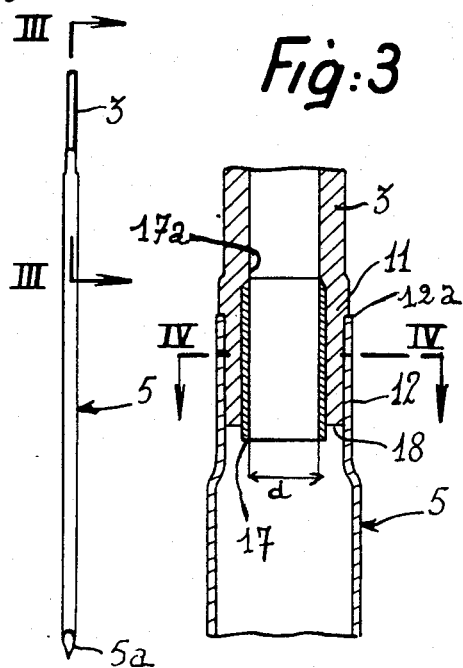

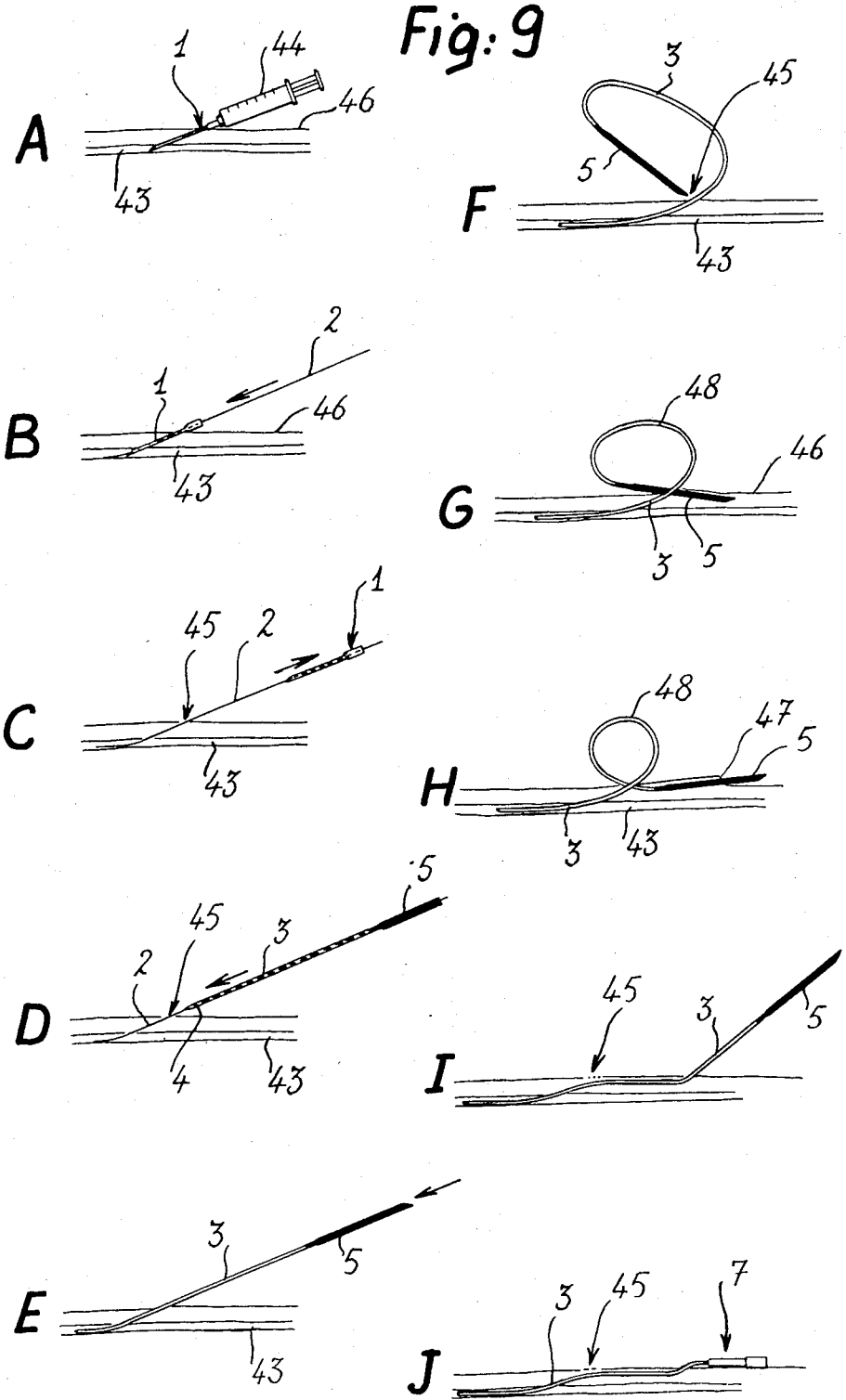

DEVICE FOR CATHETERIZATION IN PARTICULAR FOR PERFUSIONS IN THE MEDICAL AND VETERINARY FIELDS

This invention relates to a catheterization device which can be employed for perfusions in the medical and veterinary fields.

More specifically, said device comprises a flexible-tube catheter and means for "tunnelizing" the catheter tube beneath the patient's skin over a predetermined distance between a point of puncture of a blood vessel and the external surface of the patient's skin. The catheter further comprises a connector for joining the outer end of the flexible tube to an external supply pipe whilst the "tunnelization" means comprise a needle securely fixed to the end of the flexible tube and intended to be separated from this latter after tunnelization in order to permit attachment of the connector to the flexible tube.

A catheter for intravascular or peritoneal perfusions is provided with a tube which is usually flexible and intended to be introduced through the bore of a puncturing needle. A catheter of this type is well known and has been described, for example, in French Pat. No. 1,064,445.

Other types of intravascular catheters have been constructed with a view to positioning them in accordance with the technique described by Seldinger in the review entitled "Acta Radiologica" No 39, 1953, ps. 368–376. This technique consists in puncturing a blood vessel with a needle, in introducing a guide within the bore of the needle, in withdrawing the needle while leaving the guide in position, then in sliding a catheter over the guide, and finally in withdrawing the guide while leaving the catheter in position.

When these catheters are left in position in a patient during a relatively short period of time, devices of this type which have now come into standard use usually prove satisfactory. However, when it proves necessary to leave catheters of this type in position over long periods of time such as several weeks or several months, or under special environmental conditions, it is found that these catheters are liable to permit contamination of the patient by ambient germs which will enter the body through the point of initial puncture and reach the patient's vascular system. It is also observed that catheters of this type are liable to become detached either from the patient or from the perfusion tube, for example at the time of movements which the patient may make unknowingly.

In order to overcome the danger of contamination of a patient through the passageway which has been opened at the point of initial puncture, one solution consists in causing the catheter to follow, between the point of puncture of the blood vessel and the external surface of the patient's body, not the shortest path but a path of several centimeters in length and practically parallel to the patient's skin, at a distance of a few millimeters beneath the skin. Under these conditions, the external germs are obliged to travel within a substantial flesh zone which is practically not vascularized and forms a natural obstacle to their further progress. However, this so-called "tunnelization" technique calls for the use of long-nose forceps or large-size needles under conditions which often produce a traumatic effect on the patient or whicn subject catheter tubes to high stresses.

Furthermore, the different devices employed up to the present time for providing a reliable and leak-tight connection between external tubing such as a perfuser, for example, and the intravascular catheter as well as positioning of the connection on the patient's body are far from being perfect and normally make it necessary to use a large number of adhesive tapes, stitches, bandages, without offering the ease of use and speed of positioning which are required by medical practitioners.

The aim of the invention is to overcome these disadvantages by providing a catheter associated with means for "tunnelizing" the catheter tube without difficulty and for connecting said catheter to any selected external tubes with complete safety.

The "tunnelizing" means employed by the invention comprise a needle which is securely fixed to one end of the flexible tube and intended to be separated from this latter after tunnelization in order to permit attachment of the connector to the flexible tube.

However, taking into account the high pulling stresses to which the needle is subjected during the tunnelizing operation, it is necessary to ensure that said needle is very securely attached to the corresponding flexible tube without thereby producing any reduction in internal diameter of said tube.

In this connection, it is worthy of note that French Pat. No. 2,202,706 describes a device for attaching a needle to a flexible tube. This attachment is effected by crimping the corresponding extremity of said needle on the respective extremity of the corresponding flexible tube after having fitted within this latter a solid reinforcement part of malleable metal. Thus crimping of the end portion of the needle results in throttling of said solid reinforcement part and secure attachment of the needle to the flexible tube results from the deformation imposed on said tube produced by deformation and throttling of the solid internal part. Such a solution, however, cannot be contemplated for the catheterization device in accordance with the invention. Neither is it possible to adopt the solution envisaged in French Pat. No. 1,125,688 which relates to the attachment of a hollow end-piece to a flexible pipe. In actual practice, the connecting means provided in this case would not be sufficient to afford resistance to the pulling stresses exerted on a needle employed for a tunnelizing operation.

It is for the reason just mentioned that, in accordance with the invention, the needle is attached to the corresponding flexible tube by means of a fastening device comprising a rigid tube of stainless steel, for example, the internal diameter of which is equal to that of the flexible tube, said rigid tube being tightly fitted within the end of said flexible tube. The needle is provided opposite to said rigid tube with a constriction which ensures compression and clamping of the end of said flexible tube against the rigid tube without producing any reduction in internal diameter of the flexible tube. This accordingly ensures perfect attachment of said flexible tube to the tunnelization needle.

Other features of the invention will be more apparent to those skilled in the art upon consideration of the following description and accompanying drawings, wherein:

FIG. 1 is a top view showing all the elements constituting the catheterization device contemplated by the invention;

FIG. 2 is a top view to the same scale and showing the "tunnelization" needle;

FIG. 3 is an enlarged axial sectional view taken along line III—III of FIG. 2 and showing the junction zone between the flexible tube and the needle;

FIG. 4 is a transverse sectional view taken along line IV—IV of FIG. 3;

FIG. 5 is a top view of a so-called clamp for clamping the end of the flexible tube against the rigid tubular portion of the connector of the catheter on which said clamp can be mounted after completion of the tunnelizing operation;

FIG. 6 is an end view in elevation showing the clamp of FIG. 5 in the open position;

FIG. 7 is a top view of the connector of the catheter fitted with the clamp of FIGS. 5 and 6, said clamp being shown in the open position but with the rigid portion of the connector engaged within one of the half-elements of the clamp;

FIG. 8 is a view which is similar to FIG. 7 and showing the clamp which has been closed on the rigid tubular portion of the connector and secures this latter to the flexible tube which has been engaged over said rigid tubular portion;

FIG. 9 is a succession of diagrams illustrating the method for carrying out the catheterization device in accordance with the invention.

Referring to FIG. 1, there are shown all the different components of the catheterization device contemplated by the invention, viz:

a puncturing needle 1, a guide 2 consisting of a wire which is intended to be inserted in the needle 1;
a flexible tube 3 of the catheter;
a "tunnelization" needle 5 indissolubly secured to one end of the flexible tube 3;
a mandrel 6 which is intended to shut-off the bore of the needle 5;
a standardized conical connector 7 extended by a tube 8, a mandrel 9 being placed within the bore of said tube and provided with an end-fitting 10 which is intended to permit easy positioning of the tubular connector 7, 8 within the end portion of the flexible tube 3;
a clamp 13 which is intended to complete the fastening of the flexible tube 3 to the connector 7, 8 and to prevent said flexible tube from being subjected to twisting or pulling stresses.

The catheter proper is constituted by the assembly of the flexible tube 3 and of the connector 7, 8 after completion of the tunnelizing operation.

The unit formed by all the components of said device is intended to perform long-path perfusions or else to be employed in techniques of cardiovascular diagnoses.

In order to carry out this type of catheterization in actual practice, it is possible to choose a flexible tube 3 of polytetrafluoroethylene or of polyurethane or of silicone elastomer or of propylene fluoroethylene or even of polyethylene or alternatively of any other suitable plastic material which conforms to biological requirements as well as to legislation governing the medical and pharmaceutical field.

By way of numerical example without any limitation being implied, it could be decided to use for a specific requirement of perfusion flow rate or sampling rate, a flexible tube 3 of propylene fluoroethylene having an external diameter of 1.67 mm and an internal diameter of 1.07 mm.

The guide 2 which is intended to permit introduction of the flexible tube 3 can accordingly have a diameter of 0.89 mm, thus permitting easy sliding of the tube 3 which is designed to slide over the guide 2.

The end 4 of the flexible tube 3 has a suitable finish which facilitates penetration of said tube through the point of puncture of surface tissues of the blood vessel to be catheterized.

Furthermore, by virtue of the fact that the flexible tube 3 fitted with its tunnelization needle 5 must be capable of sliding over the guide 2, the needle 5 must be fixed on the tube 3 without producing any constriction of the bore of said tube to such an extent as to prevent easy penetration and sliding of the guide 2.

Thus in accordance with an essential and characteristic feature of the invention, the needle 5 is secured to the flexible tube 3 by means of a device for preventing any constriction of the bore of the tube 3 at the point of junction with the needle 5.

In the example of construction illustrated in FIG. 3, in order to join the flexible tube 3 to the needle 5 without producing any constriction of the tube bore, the device for securing the needle 5 to the flexible tube 3 comprises a rigid tube 17, the internal diameter d of which is equal to that of the flexible tube 3. The end portion 11 of the flexible tube 3 is thus tightly fitted between the rigid internal annular strengthening member 17 and the needle 5 which is provided opposite to the strengthening tube 17 with a necked portion or constriction 12, the function of which is to secure the needle 5 to the flexible tube 3 without producing any reduction in internal diameter of said tube.

This design is particularly suitable for securing a flexible tube of PTFE or of propylene fluoroethylene, taking into account the difficulties involved in bonding these materials to stainless steel.

In order to complete the numerical and non-limitative example given in the foregoing, the diameter d of the rigid tube 17 is equal to that of the flexible tube 3 and is therefore 1.07 mm, whilst the external diameter of said tube is 1.27 mm and its length is approximately 10 mm. Accordingly, the constriction 12 can have an external diameter of 2.00 mm whilst the cylindrical body of the needle 5 can have an external diameter of 2.20 mm and a length of approximately 5 to 15 mm.

If the material adopted for the flexible tube 3 consists of polyurethane, the above-mentioned internal strengthening operation, while remaining preferable, may be replaced if necessary by suitable bonding of the needle 5 which has to be secured to the flexible tube 3 in a reliable manner. The essential consideration lies in the need to ensure that the needle 5 and the flexible tube 3 are coupled together without producing any reduction in internal diameter of the tube bore to such an extent that the guide 2 would consequently no longer be capable of sliding within said bore.

Referring again to FIG. 1, there is shown in this diagram the mandrel 6 which, in order to prevent any risk of air embolism of the patient when the flexible tube 3 has been positioned within a blood vessel, is intended to shut-off the needle 5 prior to execution of the so-called "tunnelization" stage.

The mandrel 6 also serves to prevent the beveled cutting edge 5a of the needle 5 from cutting-out fragments of tissue while said needle 5 progresses beneath the patient's skin. As can readily be understood, the length and the external diameter of the obturator mandrel 6 must be chosen as a function of the position adopted for the end portion 11 of the flexible tube 3 within the constricted portion 12 of the needle 5 and also as a function of the characteristics of said needle.

In general terms, the length of the mandrel 6 must be substantially equal to the distance between that end face 18 (FIG. 3) of the flexible catheter tube 3 which is located within the interior of the needle 5 and the beveled clamping edge 5a of said needle 5.

Preferably, that end of said mandrel 6 which is intended to be applied against the portion 18 of the flexible tube 3 can be given a cross-section which is perpendicular to its axis.

On the other hand, it is usually preferable to provide a rounded finish on that end 6a of the mandrel 6 which is intended to fill the beveled edge 5a of the needle 5.

The mandrel 9, 9a which is housed within the bore of the connector 7, 8 passes through this latter entirely and that end of said mandrel which is remote from the tubular portion 8 is attached to the end-fitting 10 (as shown in FIG. 1).

The mandrel 9 is intended to facilitate positioning of the tubular connector 7, 8 within the bore of the end portion of the catheter tube 3 when this latter has been cut-off after completion of the tunnelizing operation. The body of the connector 7 is provided in known manner with two lateral lugs 16 each pierced by a hole 16a.

In accordance with an important feature of the invention, the connector 7 is fitted with a clamp 13 (as shown in FIGS. 1 and 5 to 7). By means of said clamp, the end 4a of the flexible tube 3 opposite to the end 4 which is introduced into the blood vessel is capable of clamping the rigid tubular portion 8 of the connector 7 after completion of tunnelization and separation of the needle 5 and the flexible tube 3 by cutting-off the end portion of said tube. The clamp 13 is so arranged as to prevent any relative slippage between the tubular portion 8 and the flexible tube 3 and is intended to be securely attached to the connector 7.

The clamp 13 is formed by a casing which consists of two parts or half-elements 13a, 13b, said half-elements being pivotally mounted on a hinge 26 formed, for example, by a flexible film of plastic material. These two half-elements can be closed against each other, the closure being maintained for example by means of two lugs 27 formed laterally on the half-element 13a and so designed as to engage by snap action on the ends of a corresponding projecting flange 28 which extends along the half-element 13b.

The half-element 13b of the clamp 13 is provided at that end which is directed towards the connector 7 with a flanged end 30 provided with an opening 40 through which the body of the connector 7 is permitted to pass.

The flanged end 30 is adapted to engage within an annular groove 14 formed in the end portion of the body of the connector 7 on the side nearest the tubular portion 8. The result thereby achieved is that, by closing the casing which constitutes the clamp 13, said clamp is rigidly fixed to the connector 7.

Each half-element 13a, 13b of the casing is provided internally with a pastille 21 of suitable elastic material such as a synthetic elastomer or rubber, said pastille being housed respectively within a hollowed-out portion 20 of the half-elements 13a, 13b.

Complementary grooves 22 are formed in each end of the half-elements 13a, 13b beyond the pastilles 21 in order to receive the end of the rigid tubular portion 8. Moreover, on each side of one of the grooves 22 such as, for example, the groove formed in the half-element 13b, a pair of studs 24 is so arranged as to be capable of engaging within corresponding holes 25 formed in the edges of the groove 22 of the other half-element 13a when the casing 13 is closed. Finally, the grooves 22 are provided with flared-out end portions 22a in order to prevent any damage to the flexible catheter tube 3.

When the connector 7 and its rigid portion 8 are introduced into the half-element 13b whilst the half-element 13a is open, the assembly is in the condition shown in FIG. 7: the flanged end 30 is engaged within the constricted portion formed by the groove 14 which is joined to the tubular portion 8 by means of a conical section 41, with the result that the connector 7 is locked in position against the half-element 13b. The tubular portion 8 is applied against the pastille 21 and extends within the groove 22. When the half-element 13a is pivotally displaced on the hinge 26 and then closed against the half-element 13b, the studs 24 are pressed into the corresponding holes 25; a projecting strip 42 formed at the end of the half-element 13a opposite to the flanged end 30 is applied against the connector 7, thus serving to hold the connector in position; the casing formed by the clamp 13 then closes by snap-action engagement of the lugs 27 on the ends of a portion of the flange 28.

On completion of this operation, the assembly has the general appearance shown in FIG. 8.

The method of practical application of the catheterization device described in the foregoing will now be described with reference to the diagrams of FIG. 9.

Stage A

After disinfection of the skin, the medical practitioner inserts a needle 1 in the blood vessel 43 to be catheterized such as, for example, a subclavian artery or an internal jugular vein. The needle 1 can have a length of approximately eight centimeters and is mounted on a hypodermic syringe 44 having a capacity of 10 cc.

Stages B and C

When a good blood reflux has been obtained, the practitioner withdraws the syringe 44 and introduces the spiral guide 2 into the needle 1 to a distance of about fifteen centimeters. The practitioner then removes the needle 1 (Stage C) which is then discarded.

Stage D

With the aid of a lancet, the practitioner produces a slight enlargement of the cutaneous orifice 45 through which the metallic guide 2 emerges, introduces the flexible tube 3 over said guide 2 and pushes the flexible end 4 downwards; this end is not provided with a needle but the opposite end of the tube is fitted with a needle 5. The practitioner positions the flexible tube 3 in accordance with the Seldinger method. Reference marks on the flexible tube 3 provide the practitioner with indications in regard to the length of tubing introduced.

Stage E

The practitioner withdraws the metallic guide 2, then fully inserts the obturator mandrel 6 of plastic material within the needle 5 over a distance of approximately 7 centimeters. As mentioned earlier, the mandrel 6 forestalls any danger of air embolism and prevents any possibility of cutting of fragments of the patient's tissues during the tunnelizing operation of the catheter tube 3.

Stage F

The practitioner takes hold of the needle 5 and inserts it exactly at the point of initial puncture 45 while holding the catheter in an inclined position.

Stage G

The practitioner pushes the needle 5 forward beneath the skin 46 and directs it towards the final point of emergence 47, namely the point at which the needle is intended to pass out of the skin. This stage of operation is illustrated in the diagram H.

Stage I

The practitioner withdraws the needle 5 through the emergence orifice 47 and exerts a pull on the needle while gently drawing the flexible tube 3 which is secured to the needle, this pulling action being continued until complete disappearance of the loop 48 which has formed at the initial point of puncture 45.

Stage J

The practitioner ensures that there does not exist any skin bridge beneath the catheter at the level of the initial point of puncture 45. He also makes sure that no fold has formed in the flexible tube 3 at the same level since this would be liable to interfere with the perfusion flow. The practitioner cuts the flexible tube 3 at a distance of about 1 centimeter from the crimped needle 5 which is then discarded. He adapts the socket connector 7 by inserting the assembly consisting of connector unit 7, 8 and mandrel 9 to the full extent within the flexible tube 3. The practitioner then withdraws and discards the mandrel 9 together with its end-fitting 10.

The practitioner then attaches the safety clamp 13 to the catheter as shown in FIG. 7 by engaging the flanged end 30 within the groove 14 and positioning the tubular portion 8 on the pastille 21 and within the groove 22. The clamp 13 is then closed by turning-back the half-element 13a of the clamp, by inserting the studs 24 within the holes 25 and by snap-action engagement of the lugs 27 on the flange 28. The practitioner then attaches to the patient's skin the assembly consisting of the clamp 13 and the socket connector 7, either by placing a length of adhesive tape on the clamp or by passing a thread through the holes 16a of the lugs 16. The initial puncture orifice 45 is finally closed with a skin suture.

The connector 7 can now be attached to the external tubing which has been chosen.

The catheter and the tunnelization means which have just been described offer two essential advantages: in the first place, attachment of the needle 5 to the flexible catheter tube 3 is carried out in such a manner as to prevent any reduction in diameter of the bore of said flexible tube 3 which would be liable to interfere with displacement of the guide 2 in sliding motion. In the second place, the clamp 13 is so designed as to ensure perfect fastening of the flexible tube 3 to the rigid portion 8 of the connector 7, thus preventing any relative sliding motion between these parts. As a complementary feature, the clamp 13 is very reliably secured to the connector 7 which can be detached from the clamp only by deliberate performance of an operation which consists in opening the clamp by releasing the lugs 27 of the retaining strip 28.

It will be noted that the reinforcement tube 17 must project with respect to the end face 18 of the flexible tube 3 over a minimum distance of 1 mm before forming the constriction 12. This prevents any narrowing of the bore of the flexible tube 3 at the end 18. Similarly and for the same reason, the end face 12a of the constriction 12 must be set back with respect to the end face 17a of the reinforcement tube 17.

The tunnelizing operation can be readily performed by means of the catheter in accordance with the invention and the catheter tube can be connected to any desired external tubing with complete safety.

The invention is not limited to the embodiment hereinabove described and can extend to many alternative forms of construction. Thus the clamp 13 may be constructed in any manner which is equivalent to that described in the foregoing.

What is claimed is:

1. A catheterization device which can be employed for perfusions in the medical and veterinary fields, comprising a flexible-tube catheter and means for "tunnelizing" the catheter tube beneath the patient's skin over a predetermined distanced between a point of puncture of a blood vessel and the external surface of the patient's skin, and further comprising a connector for joining the outer end of the flexible catheter tube to an external supply pipe, said connector having a hollow body provided with an extension in the form of a rigid tubular portion adapted to permit insertion of said portion within the flexible tube, wherein said connector is fitted with a clamp which is capable of tightly applying the end portion of said flexible tube against said rigid tubular portion in order to prevent any relative sliding motion between said flexible end portion and said rigid portion, said clamp being formed by a casing which consists of two half-elements pivotally mounted on a hinge, one half-element being provided at one end with a flange pierced by an opening through which the connector body is passed, said flange being adapted to fit within a groove formed in said connector body so as to ensure that the connector is securely fixed to the clamp as a result of closing of said casing.

2. A device according to claim 1, wherein each half-element of the casing is provided internally with a pastille of elastic material between which the tubular portion of the connector is clamped when the casing is closed around said tubular portion, complementary grooves being formed in the ends of the half-elements of the casing beyond said pastilles in order to receive the end of the rigid tubular portion, lugs being additionally provided on each side of one of said complementary grooves in order to engage within complementary holes of the other half-element at the time of closing of said casing.

3. A device according to claim 1, wherein the grooves are flared-out at their outer ends in order to prevent any damage to the flexible catheter tube.

* * * * *